US010039458B2

(12) United States Patent
Shimazaki et al.

(10) Patent No.: US 10,039,458 B2
(45) Date of Patent: Aug. 7, 2018

(54) PULSATION DETECTOR

(71) Applicants: Takunori Shimazaki, Kawanishi (JP); Soliton Systems K.K., Shinjuku-ku, Tokyo (JP)

(72) Inventors: Takunori Shimazaki, Kawanishi (JP); Hiroyuki Okuhata, Osaka (JP)

(73) Assignees: Takunori Shimazaki, Kawanishi-shi (JP); Solition Systems K.K., Tokyo (JP)

( * ) Notice: Subject to any disclaimer, the term of this patent is extended or adjusted under 35 U.S.C. 154(b) by 584 days.

(21) Appl. No.: 14/309,421

(22) Filed: Jun. 19, 2014

(65) Prior Publication Data

US 2014/0378780 A1   Dec. 25, 2014

(30) Foreign Application Priority Data

Jun. 21, 2013  (JP) .................................. 2013-131158

(51) Int. Cl.
*A61B 5/024* (2006.01)
*A61B 5/00* (2006.01)

(52) U.S. Cl.
CPC ...... *A61B 5/02433* (2013.01); *A61B 5/02427* (2013.01); *A61B 5/721* (2013.01); *A61B 5/6831* (2013.01)

(58) Field of Classification Search
None
See application file for complete search history.

(56) References Cited

U.S. PATENT DOCUMENTS 3,769,974 A * 11/1973 Smart ................ A61B 5/02427
                                                600/479
5,830,137 A * 11/1998 Scharf ................ A61B 5/14551
                                                600/323

(Continued)

FOREIGN PATENT DOCUMENTS

JP        5-207978 A      8/1993
JP    2004-261366 A       9/2004

(Continued)

OTHER PUBLICATIONS

European Search Report dated Oct. 29, 2014 (eight pages).

*Primary Examiner* — John R Downey
*Assistant Examiner* — Qingjun Kong
(74) *Attorney, Agent, or Firm* — Crowell & Moring LLP

(57) ABSTRACT

Disclosed is a pulsation detection system for obtaining the accurate pulsation information by removing a noise of a body motion. The system includes a beat detector obtaining a pulse wave information containing a body movement noise and a body motion information, and a pulsation detector outputting a pulsation information after the noise of the body motion is removed from the pulse wave information. The beat detector includes a pulse wave measuring device, and a body motion measuring device having a light source for irradiating light to a skin and a photodetector for detecting a reflected light from the skin, arranged at a position away from the skin. The pulsation detector includes a receiver for receiving the pulse wave information and the body motion information, and a body motion remover for removing the noise so as to output an accurate pulsation information to the output part.

1 Claim, 9 Drawing Sheets

(56) References Cited

U.S. PATENT DOCUMENTS

| | | | | |
|---|---|---|---|---|
| 6,126,595 | A * | 10/2000 | Amano | A61B 5/02 600/300 |
| 6,155,974 | A * | 12/2000 | Fish | A61B 5/0006 128/903 |
| 6,198,951 | B1 * | 3/2001 | Kosuda | A61B 5/02416 600/323 |
| 7,252,639 | B2 | 8/2007 | Kimura et al. | |
| 7,507,207 | B2 * | 3/2009 | Sakai | A61B 5/02438 600/300 |
| 8,330,596 | B2 | 12/2012 | Tanaka et al. | |
| 2008/0146890 | A1 * | 6/2008 | LeBoeuf | A61B 5/0059 600/300 |
| 2009/0156916 | A1 * | 6/2009 | Wang | A61B 5/06 600/339 |
| 2010/0198087 | A1 | 8/2010 | Takahashi et al. | |
| 2010/0249662 | A1 | 9/2010 | Shimizu | |
| 2012/0218123 | A1 * | 8/2012 | Ji | A61B 5/0022 340/870.07 |
| 2013/0060154 | A1 | 3/2013 | Morita | |

FOREIGN PATENT DOCUMENTS

| | | |
|---|---|---|
| JP | 2005-110920 A | 4/2005 |
| JP | 2005-160640 A | 6/2005 |
| JP | 2008-310630 A | 12/2008 |
| JP | 2010-172645 A | 8/2010 |

* cited by examiner

PULSATION DETECTOR

TECHNICAL FIELD

This invention relates to a pulsation detector detecting a pulsation information in movement such as playing sports.

BACKGROUND ART

Pulsation information is an information (data) obtained by removing a noise from a pulse wave information containing the noise due to body motion. Up to now, a measuring device for obtaining the pulsation information from the difference of the intensities of two reflected lights after irradiated a human arm with a light (red ($\lambda$=660 nm) and a near-infrared ray ($\lambda$=804 nm), with a use of a fact that the rate of infrared absorption of hemoglobin in a blood vessel is high, have been known (refer to Patent document 1). Also, the pulsation detector for obtaining the pulsation information, by a pulse wave sensor to detect pulse wave information based on an intensity of reflected light of an infrared light from a blood vessel of an arm, and a body motion sensor to output detection values each of 3 axis, as the body motion information, measured by 3 axis accelerometer, have been known (refer to Patent document 2).

CITATION LIST

Patent Document

[Patent document 1] JP Hei05-207978 A
[Patent document 2] JP 2010-172645 A

SUMMARY OF THE INVENTION

Problems to be Solved by the Invention

Experimental test of the device according to the patent document 1 is performed by using light sources of green light ($\lambda$=530 nm) and near-infrared light ($\lambda$=804 nm). The graph of FIG. 9(*a*) shows the 1st pulse wave information (an axis of ordinate represents mV and an axis of abscissa represents a second) obtained from the intensity of reflected light of the green light. The graph of FIG. 9(*b*) shows the 2nd pulse wave information (an axis of ordinate represents mV and an axis of abscissa represents a second) obtained from the intensity of reflected light of the near-infrared light. The graph of FIG. 9(*c*) shows the result data of pulsation information calculated on the basis of the difference of the 1st and 2nd pulse wave information (an axis of ordinate represents signal strength and an axis of abscissa represents a second). As shown in FIG. 9(*c*), the pulsation information could not be obtained. The reason of this result seems to be that the 1st and 2nd pulse wave information include not only the pulsation information but also body motion information, at different rate, respectively. Since the rate of the body motion information included in the 1st and 2nd pulse wave information is increased especially during playing sports, it is difficult to obtain accurate pulsation information.

Next, experimental test of the device according to the patent document 2 is performed. The graph of FIG. 10(*a*) shows the pulse wave information detected by the pulse wave sensor (an axis of ordinate represents mV and an axis of abscissa represents second). The graph of FIG. 10(*b*) shows the body motion information detected by the body motion sensor (an axis of ordinate represents mV and an axis of abscissa represents second). The graph of FIG. 10(*c*) shows the pulsation information calculated on the basis of the pulse wave information and body motion information (an axis of ordinate represents signal strength and an axis of abscissa represents second). As shown in figure, accurate pulsation information could not be obtained. Moreover, the information detected by the 3 axis accelerometer is an information based on the body motion of 3 axis orientation, therefore, the transition timing of the information did not correspond with that of the body motion included in pulse wave information. Thus, high correlation cannot be recognized between pulse wave information and these body motion information detected by the 3 axis accelerometer. Therefore, to obtain correct pulsation information with the device according to the patent document 2, highly advanced computing operation is needed. However, the wristwatch type pulsation detector described in the patent document 2 needs a high-speed computing processor and large-capacity battery for drive, so as to perform highly advanced computer processing in real time.

By using the technology of the patent documents 1 and 2, it is difficult to obtain the accurate pulsation information of which the noise of the body motion is removed.

An object of the present invention is to provide a pulsation detection system capable of obtaining the accurate pulsation information of which the noise of the body motion is removed even when playing active sports such as soccer.

Solution to the Problems

To solve the problem described above, the pulsation detection system of the present invention comprises a beat detector for obtaining (i) a pulse wave information containing a noise generated by a body motion and (ii) a body motion information, from a living body in physical exercise movement, and the pulsation detector detecting a pulsation information which is the pulse wave information of which the noise of the body motion is removed on the basis of the body motion information and then outputting the detected pulsation information to an output part, and wherein the beat detector comprises (a) a pulse wave measuring device detecting the pulse wave information, (b) a body motion measuring device comprising a light source and a photodetector, wherein the light source irradiates light to a skin of a living body away from the skin so as to vary an amount of a reflected light in response to a positional change of body surface due to the body motion, and wherein the photodetector detects a reflected light from the skin, synchronizing with the pulse wave information, and then, outputs a body motion information defined by the amount of the reflected light, (c) a transmitter transmitting the pulse wave information and the body motion information to the pulsation detector, (d) a mounting tool mounting the pulse wave measuring device, the body motion measuring device, and the transmitter, to a surface of the living body in physical exercise movement, and wherein the pulsation detector comprises a receiver for receiving the pulse wave information and body motion information, which are transmitted by the transmitter, a body motion remover detecting the pulsation information from the received pulse wave information and body motion information, and then outputting the pulsation information to the output port.

Preferably, the transmitter and the receiver is transceiver transmitting the information by radio signals.

Preferably, the transmitter comprises a compression unit performing compression encoding onto the body motion information on the basis of a difference between the body motion information and the pulse wave information, a multiplexer generating a series of packet data by multiplexing the pulse wave information and the compression code, and a transceiver transmitting the packet data, and wherein the receiver comprises a transceiver receiving the packet data, a demultiplexer demultiplexing the received packet data and then outputting separated datum of the pulse wave information and the compression code, and a decoder outputting the body motion information decompressed from the pulse wave information and the compression code, and wherein the pulse wave information outputted from the demultiplexer and the body motion information outputted from the decoder, are outputted to the body motion remover.

Preferably, the pulse wave measuring device, the body motion measuring device, the transmitter of the beat detector are put into one case, and it can be attached to the living body in physical exercise movement, by a belt or an adhesion attachment.

Preferably, the pulsation detection system comprises several beat detectors and one pulsation detector having the output part, wherein the pulsation detector receives the packet data from the beat detectors in order, and thereby detects the pulsation information from the packet data to carry out a list output of the detected pulsation information to the output part.

Preferably, the transceiver of the beat detector is connected with a monitor monitoring the pulsation as the output part, and the body motion remover of the pulsation detector makes the monitor display the pulsation information via both of the pulsation detector of the receiver and the transceiver of the beat detector.

Effects of the Invention

The pulsation detection system of the present invention obtains a accurate body motion information by the body motion measuring device which obtains the body motion information indicating the amount of movement of the skin due to the body motion on the basis of the intensity of reflected light generated by the light source irradiating with light from the position away from a skin of a living body. Thereby, the pulsation detection system is capable of removing the noise of the body motion contained in the pulse wave information, and the accurate pulsation information can be obtained.

BRIEF DESCRIPTION OF THE DRAWINGS

FIG. 9(a) is a graph showing a pulse wave information obtained by an intensity of the reflected light generated by an irradiation of green LED light, and FIG. 9(b) is a graph showing a pulse wave information obtained by an intensity of the reflected light generated by an irradiation of red LED light, and FIG. 9(c) is a graph showing a pulsation information obtained by an operation using two pulse wave information.

FIG. 10(a) is a graph showing a pulse wave information obtained by an intensity of the reflected light of LED light, and FIG. 10(b) is a graph showing a body motion information detected by means of a 3 axis accelerometer, and FIG. 10(c) is a graph showing a pulsation information obtained by operation using the pulse wave information and the body motion information.

DETAILED DESCRIPTION

Figure 1:
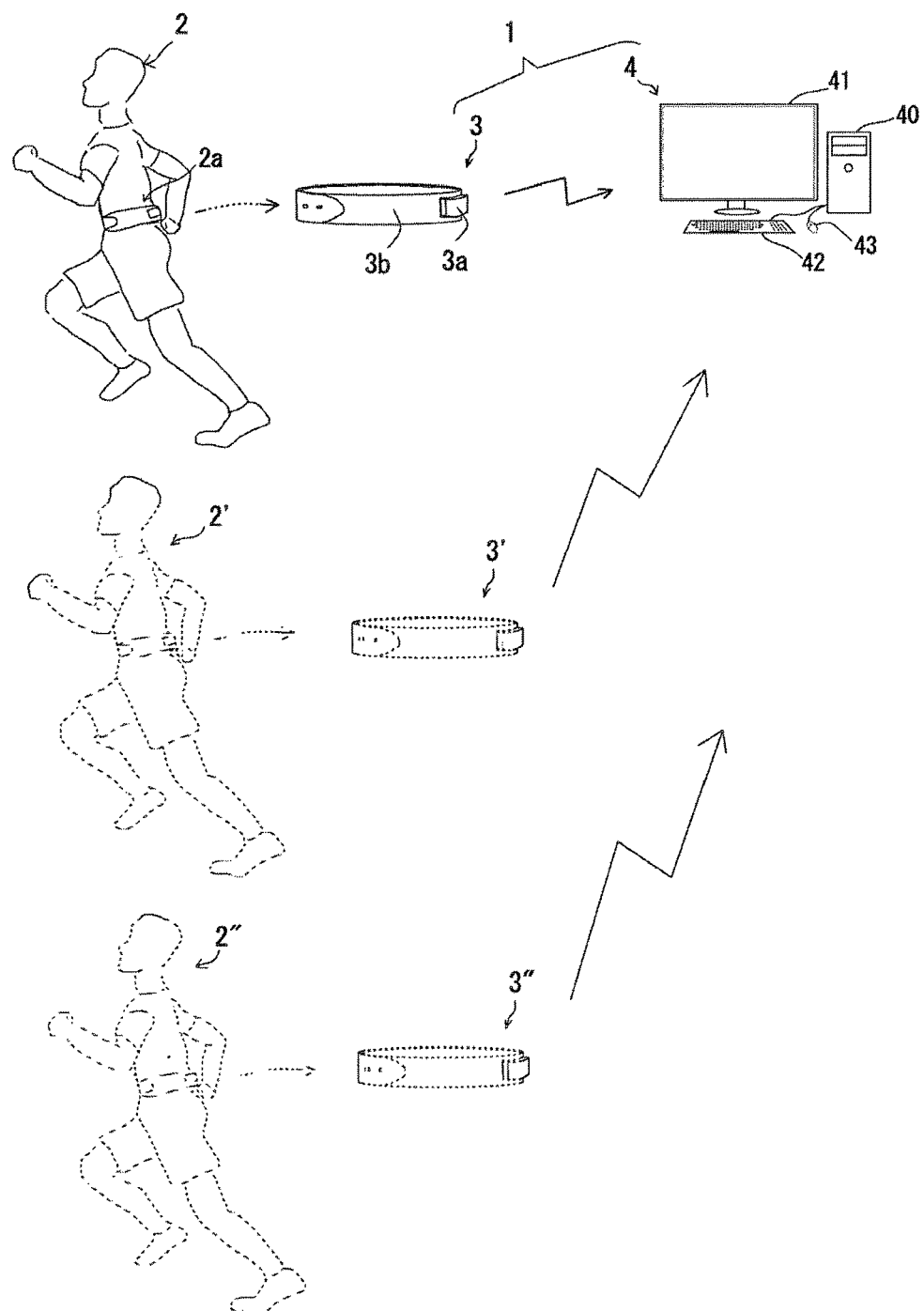
FIG. 1 is an entire configuration figure of the pulsation detection system according to first embodiment.

This invention is based on an experimental result that precise data of a pulsation information can be detected on the basis of a body motion information indicating a degree of positional change of a skin due to the body motion, wherein the body motion information is detected from amount of a reflected light of LED light irradiating at a position away from (for example, away 0.5 mm or more) the skin. The pulsation detection system comprises a beat detector and a pulsation detector, wherein the beat detector measures a pulse wave information containing the noise generated by a body motion and body motion information, and wherein the pulsation detector detects a pulsation information of which a noise generated by a body motion is removed from the pulse wave information based on the body motion information. The body motion information is varied at the same timing as a fluctuation information caused by the body motion contained in the pulse wave information obtainable on a basis of amount of reflected light obtained when a light such as near-infrared rays is irradiated toward the blood vessel of human arm by using a directional LED light. Therefore, by easy computer processing, the pulsation detector can detect the pulsation information from the pulse wave information and the body motion information, and outputs the detected pulsation information. Since the pulse wave information is similar to the body motion information, the pulse wave information and body motion information can be compressed to packet data. Thereby, a wire or wireless high-speed data transfer can be established among several beat detectors and one pulsation detector, so, real-time management of pulsation information of several members can be achieved.

A pulsation detection system 1 according to the first embodiment is explained in detail, hereinafter. A beat detector 3 is used to a runner 2 under exercise, and measures pulse wave information and body motion information. A pulsation detector 4 obtains a pulsation information on the basis of the measured pulse wave information and body motion information. In addition, as shown with a dotted line, one pulsation detector 4 can perform a batch management of several beat detectors 3' and 3" attached to the runners 2' and 2".

As shown in FIG. 1, the beat detector 3 comprises a battery-operated device body 3a and a belt type mounting tool 3b which attaches the device body 3a to a waist 2a of the living body's surface, for example, a runner in movement. A mounting method of the mounting tool 3b can use an adhesion type instead of a belt type. A position to which the detector 3 is attached is a position where the pulse wave can be easily detected from a subcutaneous part blood vessel, for example, near a vein at a shallow position from a skin surface (for example, near the backbone of the waist etc.). The pulsation detector 4 comprises a main part 40, an output part 41, a key-board 42, and a mouse 43, wherein the main part 40 performs wireless communications and computing operations, the output part 41 have a monitor monitoring the pulsation information, the key board 42 is used for inputting or setting, and the mouse 43 is a pointing device. A main part 3a of the beat detector 3 has a unique ID, and performs data communication by using packet data, after the main part 3a establishes connection to the main part 40 of the pulsation detector 4.

Figure 2:
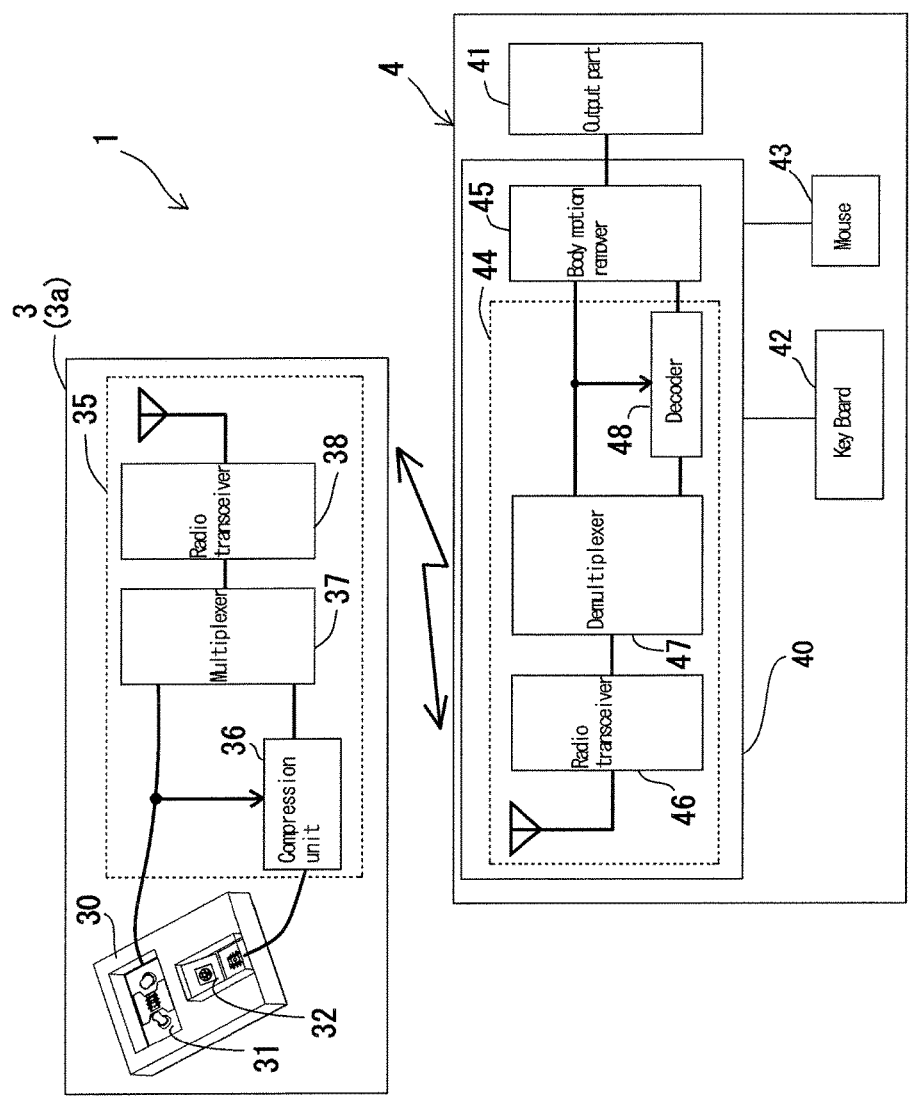
FIG. 2 is a block diagram showing each function of the pulsation detection system.

As shown in FIG. 2, the main part 3a of the beat detector 3 comprises the pulse wave measuring device 31, a body motion measuring device 32 and a transmitter 35, wherein the device 31 detects a pulse wave information including a pulsation information and a noise generated by the body motion, and wherein these are all driving by battery power source (not shown). The main part 40 of the pulsation detector 4 comprises a receiver 44 and a body motion remover 45.

Figure 3:
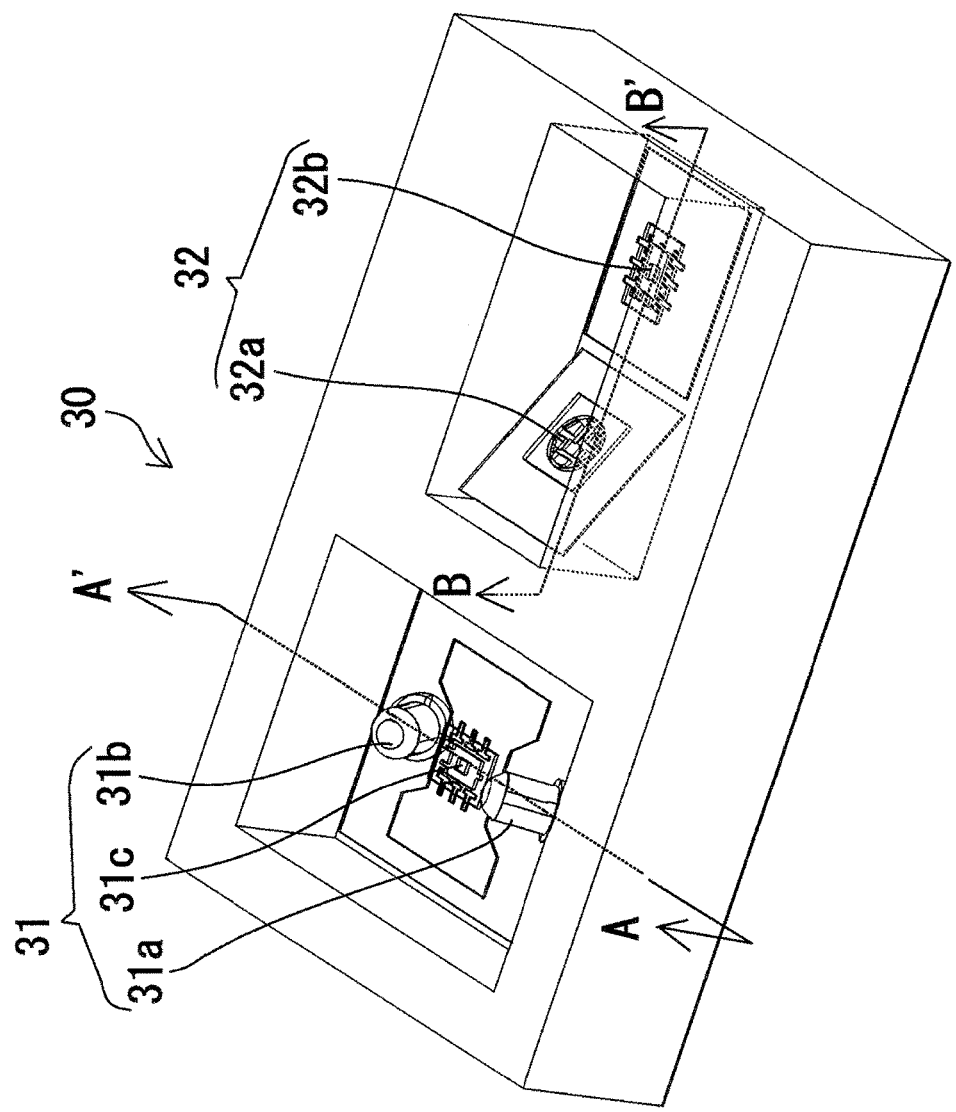
FIG. 3 is a perspective diagram showing the beat detector of the pulsation detection system.
Figure 4:
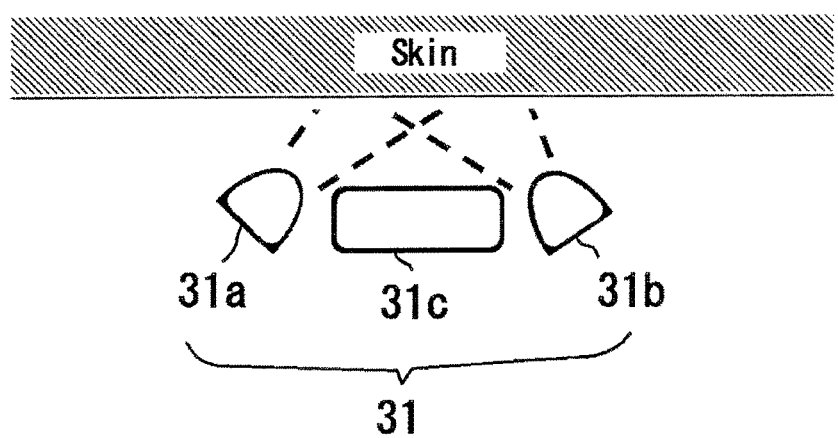
FIG. 4 is A-A' sectional view of FIG. 3.
Figure 5:
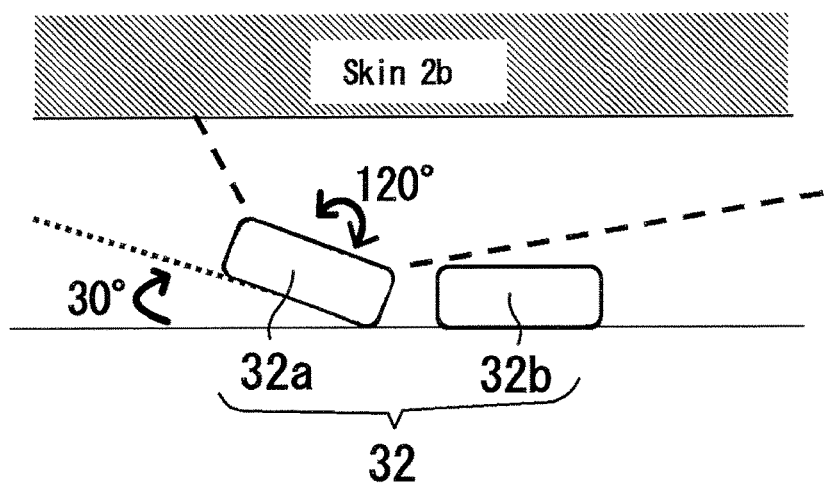
FIG. 5 is B-B' sectional view of FIG. 3.

The structure of the pulse wave measuring device 31 of the beat detector 3 and the body motion measuring device 32 is explained hereinafter. FIG. 3 to FIG. 5 show the pulse wave measuring device 31 and the body motion measuring device 32, wherein the devices 31, 32 are mounted in the concave portions of rectangular resin-made case 30 of which longitudinal length is about 50 mm, width is about 30 mm, and height is about 15 mm. In addition, the size of the case 30 can be smaller when condition is satisfied in relation to the distance between the skin and the pulse wave measuring device 31 and the body motion measuring device 32, and the mutual layout, as explained below.

The pulse wave measuring device 31 comprises two light sources 31a, 31b for pulse wave, wherein the two light source 31a, 31b are irradiate green light to a target blood vessel of a living body, and a photodetector 31c for pulse wave arranged at a position where the reflected green light can be detected. The change of the intensity of reflected light indicates the degree of positional change of skin position due to the body motion, i.e. the body motion information. In the pulse wave measuring device 31, the light sources 31a, 31b for pulse wave and/or the photodetector 31c for pulse wave are positioned close to the skin as much as possible, so that the amount of detection of the reflected light from the skin is minimized, and only the reflected light from the blood vessel under the skin is mainly detected.

As shown in A-A' sectional view of FIG. 4, the two light sources 31a, 31b for pulse wave of the pulse wave measuring device 31 are positioned at the elevation angle of about 50 to 60 degrees toward the skin 2b of a target. The light sources 31a, 31b for pulse wave comprising LED that is, for example, artilleryshell type LED manufactured by A-Bright company (Type No. AL-314UG 2C-A (green λpeak=530 nm)), wherein the diffusion angle is 30 degrees, and diameter is about 3.2 mm. The photodetector 31c for pulse wave is positioned between the two light sources 31a, 31b, and the photodetector 31c uses, for example a digital color sensor (color sensor S9706 manufactured by Hamamatsu Photonics, Inc.). The two light sources 31a, 31b and the pulse wave photodetector 31c are positioned at about 0.2 mm to 0.5 mm of distance from the skin 2b, for example. The pulse wave information detected by the pulse wave measuring device 31 contains the noise of reflected light from the skin, generated by the body motion.

The body motion measuring device 32 comprises a body motion light source 32a and a body motion photodetector 32b, wherein the light source 32a irradiates a diffused light at a position away from the skin 2b of the living body, and the photodetector 32b is positioned away from the skin 2b, and detects the degree of positional change of the skin on the basis of the amount of reflected light from the skin 2b, synchronizing with the pulse wave information. The degree of positional change of the skin indicates the body motion information showing a degree of the positional change of the body surface due to body motion. The body motion light source 32a is a LED (for example, [LK-1PG-6] (green) made by EK-Japan) of a 120 diffusion angles, in a rectangular parallelepiped shape and with a planar surface, wherein the LED is positioned at 30 angles of elevation toward the skin 2b, as shown in sectional view in B-B' of FIG. 5. By using the LED which irradiates with the wider range than the photodetection surface of the photodetector 32b, the pulse wave information slightly included in the amount of reflected light is averaged, thereby it seems that the body motion information can be detected more efficiently. The body motion photodetector 32b is arranged at a position where the reflected light generated by the light source 32a can be detected, wherein the photodetector 32b uses a digital color sensor of about 4 mm square (for example, color sensor S9706 by Hamamatsu Photonics, Inc.). The angle of elevation of the body motion light source 32a, the position of the photodetector 32b and the distance from the photodetector 32b to the skin 2b described above, are one example of embodiments, they should be set as appropriate value to obtain the strongest body motion information on the basis of the experimental data, practically.

The body motion light source 32a and the body motion photodetector 32b are arranged at a position away from the skin 2b so that the amount of the reflected light varies in response to the degree of the positional change of the body surface due to the body motion. Specifically, the body motion light source 32a and the body motion photodetector 32b are arranged at a position (1 mm, 2 mm, etc.) away from the skin 2b, for example, more than 0.5 mm, so as to mainly detect the amount of the reflected light from the skin 2b, and not to detect or merely detect the amount of the reflected light from the blood vessel under the skin 2b so that the reflected light from the blood vessel does not affect processing. Although it changes with the luminescence intensity of the light source 32a, the pulse wave information which affects pulsation detection was not included in the detection value measured at the position away from the skin 2b about 0.5 mm more, practically. The body motion information obtained by the body motion measuring device 32 of abovementioned structure has the same transition timing as the fluctuation information caused by the body motion recognized as a noise, within the pulse wave information detected by the pulse wave measuring device 31, and has a different amplitude but similar shape data.

The pulse wave measuring device 31 and the body motion measuring device 32 are installed in the case 30 under the conditions that misdetection of the reflected light of the light irradiated from the pulse wave light source 31a, 31b are not carried out with the body motion photodetector 32b, also misdetection of the reflected light of the light irradiated from the body motion light source 32a is not carried out by the pulse wave photodetector 31c. Specifically, there is a sufficient distance or a wall between the pulse wave measuring device 31 and the body motion measuring device 32 so as to prevent misdetection. As shown in FIG. 3, the light-emitting direction of the pulse wave light sources 31a, 31b are arranged as the direction intersecting perpendicularly with the direction toward the body motion measuring device 32 in the experiment. Also, the distance between the pulse wave light sources 31a, 31b and the body motion photodetector 32b, and also the distance between the pulse wave photodetector 31c and the body motion light source 32a are separated about 20 mm. The luminescence intensity of the light sources 31a, 31b and 32a are adjusted just before the start of experiment so that signal amplitudes of the pulse wave information obtained by the pulse wave measuring device 31 and the body motion information obtained by the body motion measuring device 32 come to the same value. Thereby, the desirable detection value has been obtained (see FIG. 7(c)).

Figure 6:
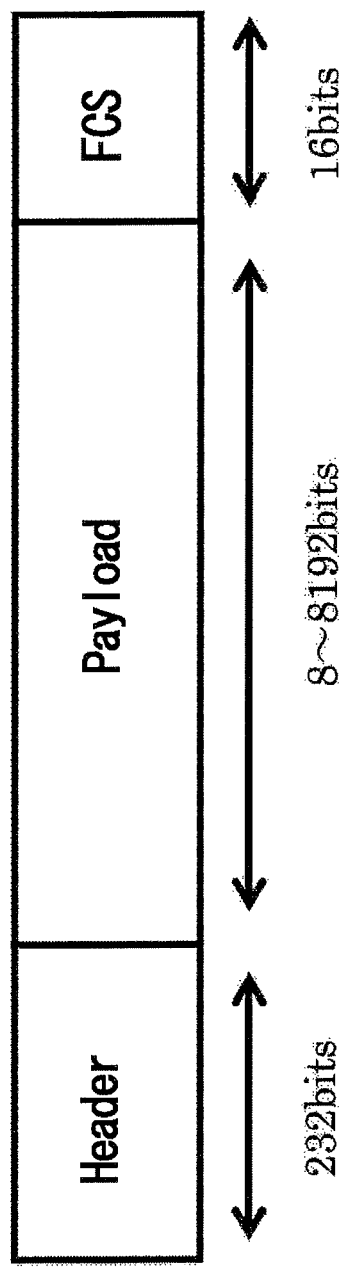
FIG. 6 is a block diagram showing the structure of packet data which is outputted to a radio transceiver of the pulsation detector from the radio transceiver of the beat detector.

The structure of the transmitter 35 of the main part 3a of the beat detector 3 is explained hereinafter with reference to FIG. 2. The transmitter 35 comprises a compression unit 36, a multiplexer 37, and a radio transceiver 38. A body motion information detected by the body motion measuring device 32 has a similar shape data in comparison with a fluctuation information caused by the body motion contained in the pulse wave information as a noise. The compression unit 36 compresses the difference of the pulse wave information and the body motion information by a well-known run length (Huffman) coding etc. The multiplexer 37 generates and outputs a series of packet data containing a 232-bit header, the pulse wave information and compression code (between 8-bit to 8192-bit), and a 16-bit FCS (Frame Check Sequence), as shown in FIG. 6. The radio transceiver 38 has a unique ID, and establishes a connection by means of a predetermined protocol, for example, a connection-oriented protocol, and then sends out packet data towards the receiver 44.

The structure of the main part 40 of the pulsation detector 4 is explained hereinafter with reference to FIG. 2. The receiver 44 comprises a radio transceiver 46, a demultiplexer 47, and a decoder 48. Between the radio transceiver 38 of the beat detector 3 and the radio transceiver 46, the radio transceiver 46 establishes bidirectional connection by checking a unique ID pre-assigned by a protocol based on e.g. IEEE802.11 standard, and then it transmits and receives the packet data. Each of the radio transceivers 38 and 46 has a transmitting function of a radio signal required to establish a connection. The demultiplexer 47 separates the received packet data into a pulse wave information and a compression code, and outputs them. The decoder 48 decodes the body motion information from the pulse wave information and the compression code, outputted from the demultiplexer 47, and then outputs the body motion information.

By using these characteristics, and also by the pulse wave information outputted from the demultiplexer 47, the body motion information outputted from the decoder 48, and the adaptive filter, the body motion remover 45 detects a pulsation information by removing a noise from the pulse wave information containing the noise due to a body motion, and then outputs the pulsation information to the output part 41. As described above, the body motion information has the same transition timing of the fluctuation information caused by the body motion contained in the pulse wave information as a noise, and has a different amplitude but similar shape data. The adaptive filter (e.g. RLS type, the oblivion coefficient $\lambda=0.97$, number of taps Tap=8) changes the amplitude and phase of the body motion information accommodatively so that the amplitude and phase of the body motion information is matched to that of the noise due to the body motion contained in the pulse wave information, and the noise is removed from the pulse wave information. Because the accurate body motion information can be obtained, it is enable to filter more accurate pulse wave information only by the adaptive filter using the well-known noise cancellation technology, compared with a band pass filter which removes the changed body motion information from the pulse wave information after changing the amplitude and phase of the body motion information evenly.

In one embodiment, the output part 41 uses a monitor monitoring the pulsation. Also the output part 41 may use the other output methods to visualize and output the detected pulsation information as a numerical value, a graph, and an image, for example, a printer. Also, the output part 41 may change and output contents of pulsation as sound with a fast/slow tempo or a high/low tone, and LED showing flickering times of the flash light per hour and etc. based on the detected pulsation information.

Figure 7:
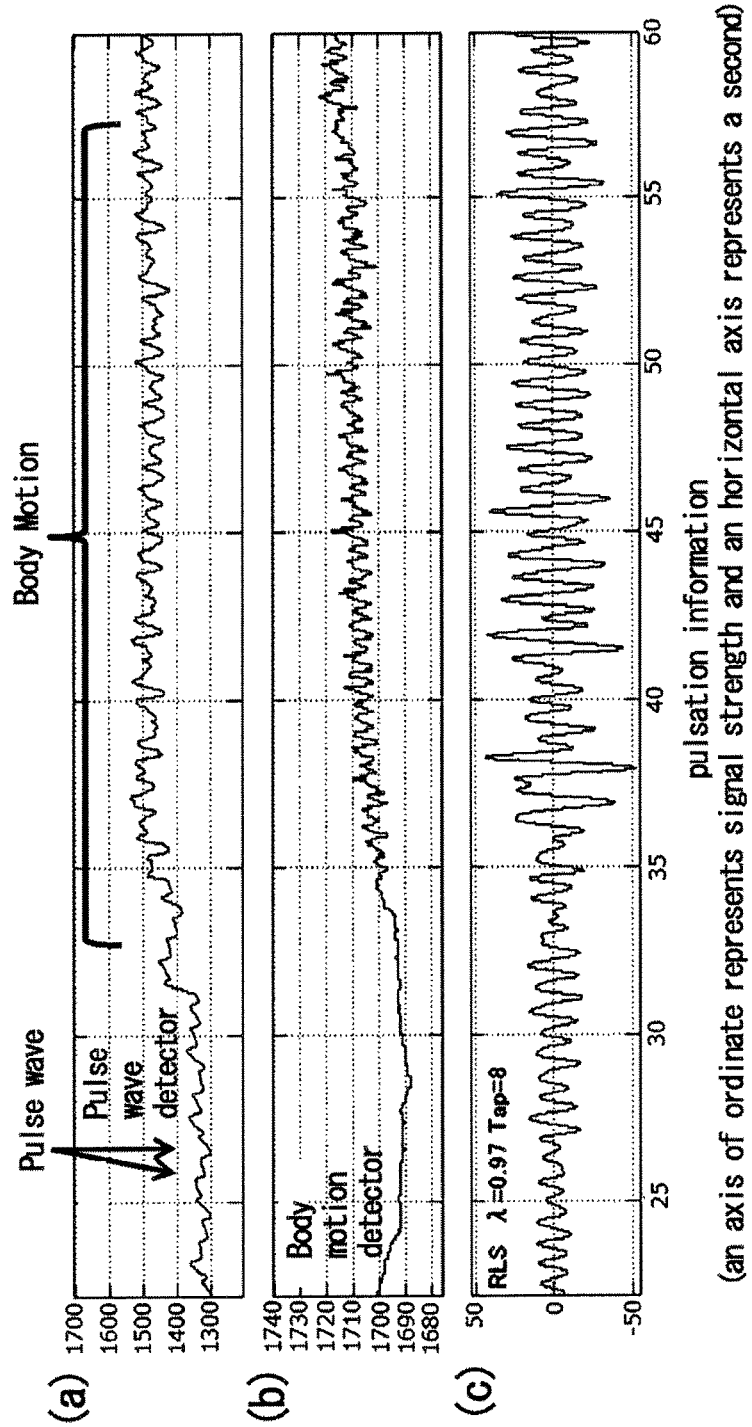
FIG. 7(a) is a graph showing the pulse wave information, which is outputted from the pulse wave measuring device, containing the noise generated by the body motion.
FIG. 7(b) is a graph showing the body motion information outputted from the body motion measuring device.
FIG. 7(c) is a graph showing the pulsation information outputted from the body motion remover.

The graph of FIG. 7(a) shows the pulse wave information (an axis of ordinate represents mV and an horizontal axis represents a second) containing the noise due to a body motion, the graph of FIG. 7(b) shows body motion information (an axis of ordinate represents signal strength and an horizontal axis represents a second), and the graph of FIG. 7(c) shows pulsation information (an axis of ordinate represents signal strength and an horizontal axis represents a second). The body motion information has the same transition timing of the fluctuation information caused by the body motion contained in the pulse wave information, and has a different amplitude but similar shape data. By using this body motion information, the accurate pulsation information (an axis of ordinate represents signal strength and an horizontal axis represents a second) can be obtained, wherein only the noise due to a body motion is removed from the pulse wave information by an adaptive signal processing.

As described above, in the pulsation detection system 1, the pulsation information can be detected from the pulse wave information and the body motion information by easy computing operation, and then it can be outputted to the output unit 41.

The beat detector 3 has a unique ID for establishing the packet communication, and the pulsation detector 4 can recognize two or more beat detectors based on this unique ID. Therefore, as shown with a dotted line in FIG. 1, the pulsation detection system may be constituted several beat detectors 3, 3', and 3", and one pulsation detector 4. In this case, several beat detectors 3, 3', and 3" are mounted to the players 2, 2', and 2", playing sport, such as soccer. The pulsation detector 4 establishes bidirectional connection to these beat detectors 3, 3' and 3" in order, and then receives packet data, and thereby detects each pulsation information, and then outputs a list result on the display screen of the output unit 41. The list result may be respectively displayed pulsation information of each individual player on several rectangular screens divided from the display screen. This display processing can be performed in real time, because the body motion measuring device 32 can obtain the body motion information similar to the pulse wave information and thereby the compression code of the body motion information can be transmitted in form of the packet data. As a result, for example, the coach of a soccer team can perform batch management of each player's pulsation information during a game by checking the output unit 41 of the pulsation detector 4.

The Second Embodiment

Figure 8:
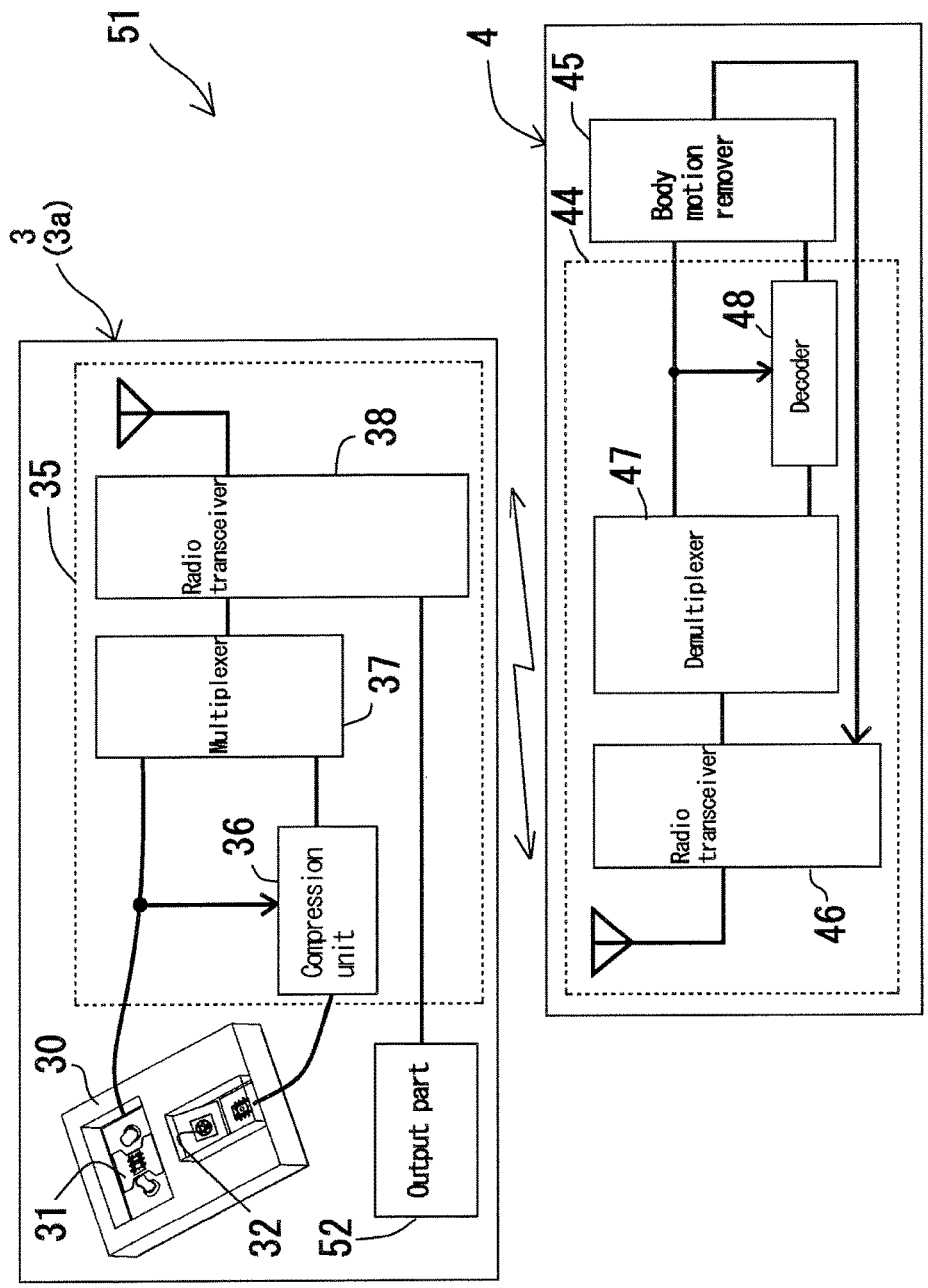
FIG. 8 is an entire configuration figure of the pulsation detection system according to 2nd Embodiment.
Figure 9:
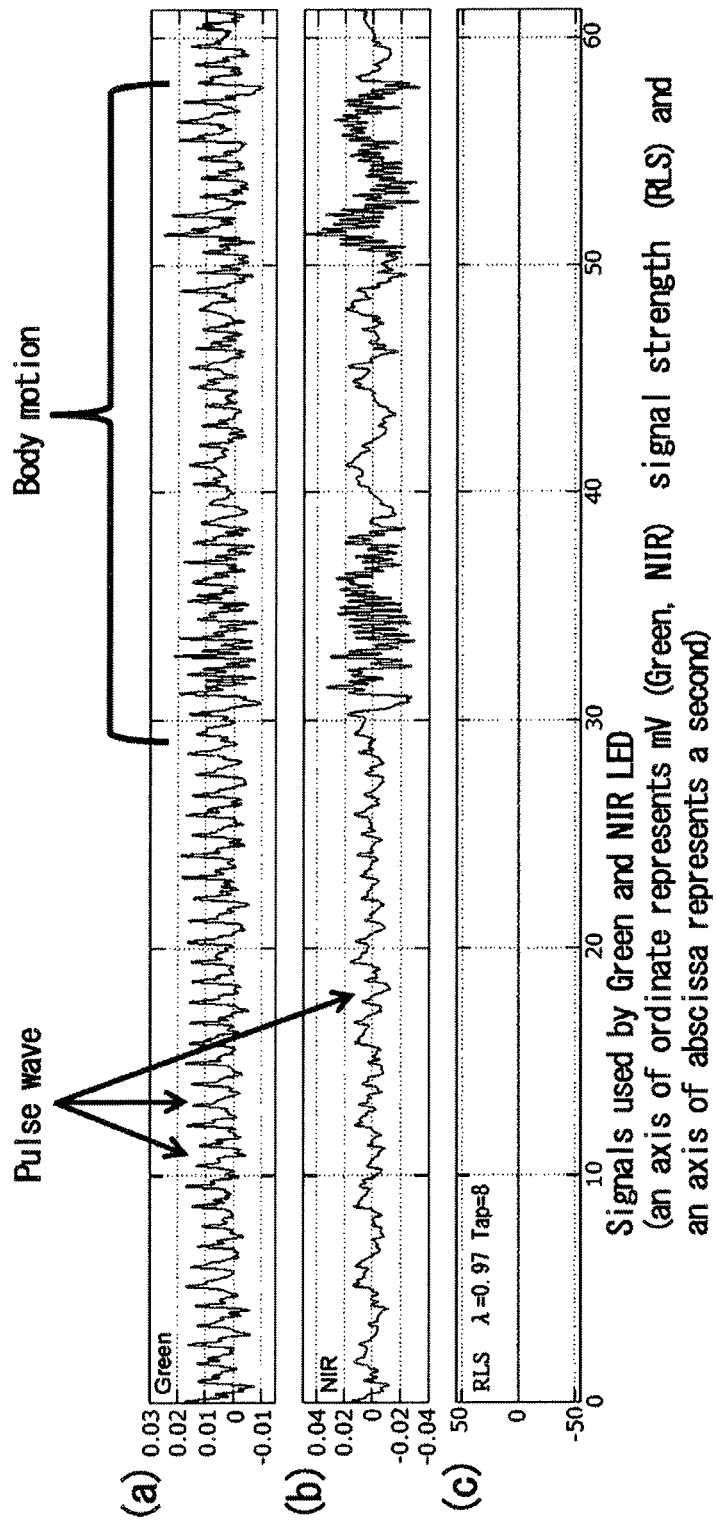
FIG. 9 shows a conventional test result.
Figure 10:
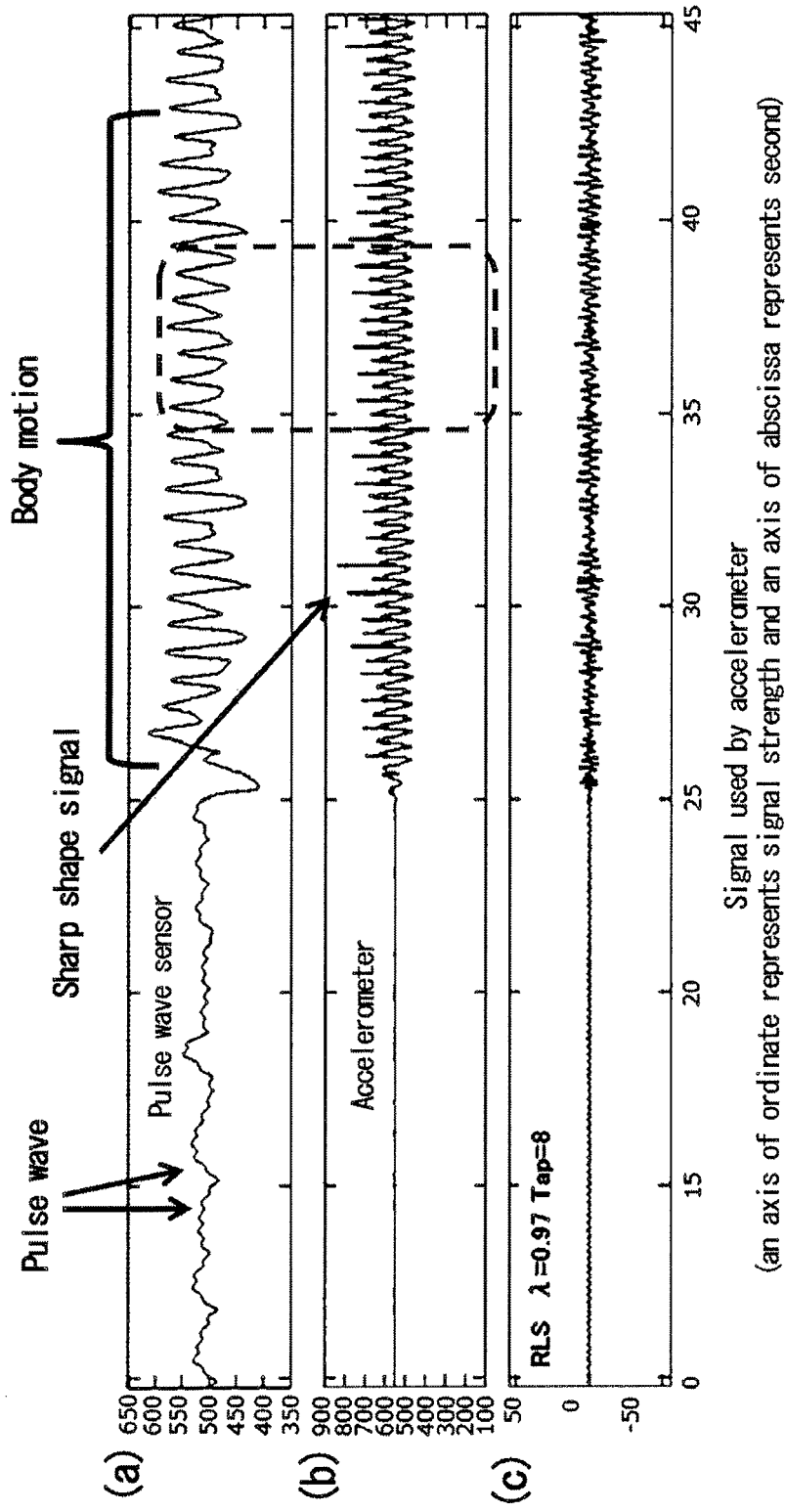
FIG. 10 shows a conventional test result.

FIG. 8 shows the structure of a pulsation detection system 51 according to the second embodiment. The same reference numbers are used for the same component of the pulsation detection system 1 of the first embodiment in this figure in order to omit the same explanation. In the pulsation detection system 51, an output part 52 is equipped to the beat detector 3 instead of or in addition to the output part 41, the keyboard 42, and the mouse 43 of the pulsation detector. This output part 52 (monitor) is connected to the radio transceiver 38 of the beat detector 3, and acts as a monitor monitoring the pulsation. In detail, the output terminal of the body motion remover 45 of the pulsation detector 4 is connected to the output part 52 through the radio transceiver 46 of the pulsation detector 4 and the radio transceiver 38 of the beat detector 3.

The output part 52 is a clock-type display device or a sound generator, attached to the arm of the living body during motion, for example, jogging. Wherein the display device has a liquid-crystal-display part which indicates pulsation information, and the sound generator indicates a state of the pulsation information by a sound with corresponding tempo or tone.

Modification of the Second Embodiment

As a modification of the pulsation detection system 51 of the second embodiment, the output part 52 can afford to comprise, a Radio Communications part based on IEEE standard e.g., a liquid-crystal-display part displaying the pulsation information, and a wristwatch-type computer or tablet computer with a small built-in battery. In this case, the output part 52 establishes a connection to the radio transceiver 46 of the pulsation detector 4 by the protocol which is in conform to the IEEE802.11 standard e.g., by the function of the Radio Communications part, and exchanges packet information, and then displays the pulsation information.

In addition, the pulsation detector according to the present invention is not limited to the above embodiments and the modification thereof, and may be modified in various manners. For example, the light source 32a of the body motion measuring device 32 of the first embodiment uses a LED emitting the light of 120 diffusion angles. However, a laser or LED with a narrow diffusion angle of light, or a LED with a wide diffusion angle of light can be used, if the photodetector 32b can receive enough reflected light indicating body motion information.

Also, the pulsation detector 4 may omit the keyboard 42 and the mouse 43, when unnecessary, or when a touch panel and a software keyboard are used as the output part 41. Also, the beat detector 3 may be connected with the pulsation detector 4 by the cable. In this case, accurate and high-speed pulsation detection processing is realized without the influence of an outer radio noise.

INDUSTRIAL APPLICABILITY

Since the pulsation detection system of the present invention needs less amounts of 1 packet data both of the pulse wave information and the body motion information, not only the case of a cable communication, but the case of wireless communications, high-speed pulsation detection can be performed. Therefore, this invention can be applied to a various sports and medical fields requiring the real-time operation. Furthermore, an electrocardiograph for obtaining an accurate electrocardiogram of which the noise by the body motion has been removed, can be provided, if the electrocardiograph of which process the electrocardiogram containing the noise is used instead of the pulse wave measuring device of the pulsation detection system of the present invention.

DESCRIPTION OF THE REFERENCE CHARACTERS

1 and 51 Pulsation Detection System
2, 2', and 2" Runner (living body during motion)
3, 3', and 3" Beat detector
3a and 40 Main part
3b Mounting tool
31 Pulse Wave Measuring Device
32 Body Motion Measuring Device
35 Transmitter
36 Compression unit
37 Multiplexer
38 and 46 Radio transceiver
31a and 32a Light source
31c and 32b Photodetector
4 Pulsation Detector
44 Receiver
45 Body Movement Remover
47 Demultiplexer
48 Decoder
41 and 52 Output part

The invention claimed is:

1. A pulsation detection system comprising,
a beat detector configured to be mounted to a body for obtaining (i) a pulse wave information containing a noise generated by a body motion and (ii) a body motion information, from the body in physical movement, and
a pulsation detector for detecting a pulsation information which is obtained by removing the noise of the body motion from the pulse wave information based on the body motion information and then outputting the detected pulsation information to an output part, wherein
the beat detector comprises,
(a) a pulse wave measuring device for detecting the pulse wave information, the pulse wave measuring device including pulse wave light sources for irradiating light to the body, and a pulse wave photodetector for detecting the light reflected from the body,
(b) a body motion measuring device for detecting the body motion information, the body motion measuring device including a body motion light source for irradiating light to a skin of the body, and a body motion photodetector for detecting the light reflected from the skin,
(c) a transmitter for transmitting the pulse wave information and the body motion information to the pulsation detector, and
(d) a mounting tool for mounting the pulse wave measuring device, the body motion measuring device, and the transmitter, to the body, wherein
the lights irradiated from the pulse wave light sources and the body motion light source have a same green color;

the body motion light source is positioned farther from the skin than the pulse wave light sources, and the body motion photodetector is positioned farther from the skin than the pulse wave photodetector, and the pulsation detector comprises, a receiver for receiving the pulse wave information and the body motion information which are transmitted by the transmitter, and a body motion remover for removing the noise to detect the pulsation information from the received pulse wave information and body motion information, and then outputting the pulsation information to the output part.

* * * * *

UNITED STATES PATENT AND TRADEMARK OFFICE
CERTIFICATE OF CORRECTION

| | | |
|---|---|---|
| PATENT NO. | : 10,039,458 B2 | Page 1 of 1 |
| APPLICATION NO. | : 14/309421 | |
| DATED | : August 7, 2018 | |
| INVENTOR(S) | : Takunori Shimazaki et al. | |

It is certified that error appears in the above-identified patent and that said Letters Patent is hereby corrected as shown below:

On the Title Page

Item (73), Correct the second Assignee Name to reflect -- Soliton Systems K.K. --.

Signed and Sealed this
Sixteenth Day of November, 2021

Drew Hirshfeld
*Performing the Functions and Duties of the
Under Secretary of Commerce for Intellectual Property and
Director of the United States Patent and Trademark Office*